United States Patent [19]

Peglion et al.

[11] Patent Number: 5,726,208

[45] Date of Patent: Mar. 10, 1998

[54] HETEROCYCLIC TERTIARY AMINES

[75] Inventors: Jean-Louis Peglion, Le Vesinet; Bertrand Goument, Viroflay; Jean-Christophe Harmange, Saint Germain en Laye; Joel Vian, Chaville; Aimée Dessinges, Thiais; Mark Millan, Le Pecq; Valérie Audinot, Croissy, all of France

[73] Assignee: Adir et Compagnie, Courbevoie, France

[21] Appl. No.: 728,759

[22] Filed: Oct. 11, 1996

[30] Foreign Application Priority Data

Oct. 13, 1995 [FR] France ................. 95 12044

[51] Int. Cl.[6] .............. A61K 31/135; A61K 31/165; C07C 211/43; C07D 335/08

[52] U.S. Cl. .................. 514/656; 514/619; 514/437; 514/443; 514/454; 514/470; 564/427; 564/168; 549/26; 549/27; 549/43; 549/46; 549/48; 549/393; 549/394; 548/486

[58] Field of Search .................. 564/427, 168; 514/656, 619, 437, 443, 454, 470; 549/26, 27, 43, 46, 48, 393, 394; 548/486

[56] References Cited

U.S. PATENT DOCUMENTS

| | | | |
|---|---|---|---|
| 4,062,840 | 12/1977 | van der Burg | 544/111 |
| 4,105,785 | 8/1978 | Mauvernay et al. | 421/285 |
| 4,470,990 | 9/1984 | Asselin et al. | 424/267 |
| 4,863,951 | 9/1989 | Peglion et al. | 514/422 |
| 4,904,688 | 2/1990 | Rae et al. | 514/450 |
| 5,071,858 | 12/1991 | Hutchison | 514/324 |
| 5,141,960 | 8/1992 | Cordi et al. | 514/619 |
| 5,189,065 | 2/1993 | Czech et al. | 514/656 |
| 5,276,053 | 1/1994 | Johnson | 514/437 |
| 5,538,986 | 7/1996 | Ting et al. | 514/337 |

*Primary Examiner*—Deborah Lambkin
*Attorney, Agent, or Firm*—Gordon W. Hueschen

[57] ABSTRACT

New compounds of formula:

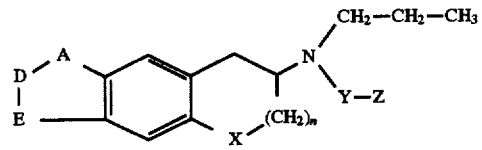

wherein:

—A—D—E, X, n, Y and Z are as defined in the description, in racemic form and in the form of optical isomers, and their addition salts with pharmaceutically acceptable acids.

Those compounds may be used as medicaments.

7 Claims, No Drawings

HETEROCYCLIC TERTIARY AMINES

The present invention relates to new heterocyclic tertiary amines, a process for their preparation and pharmaceutical compositions containing them.

It relates more especially to compounds of formula I:

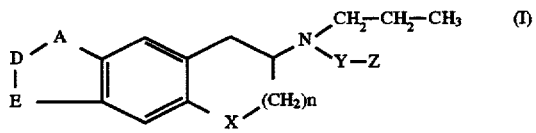

wherein:

—A—D—E— represents

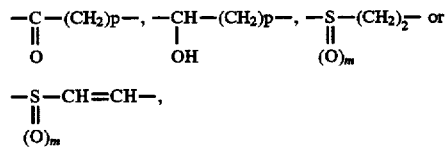

p represents 2 or 3 and
m represents zero, 1 or 2;
X represents:
  a —$CH_2$— group and also,
  when —A—D—E— represents

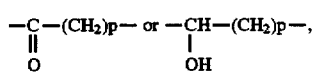

X may also represent an oxygen atom;
n represents:
  zero or 1 when X represents a $CH_2$ group and solely 1 when X represents an oxygen atom;
Y represents a single bond or a —$CH_2$— group, and
Z represents:
  an alkyl, alkenyl or alkynyl radical, each containing up to 10 carbon atoms inclusive in straight or branched chain and each optionally substituted by one or more cycloalkyl radicals each having from 3 to 7 carbon atoms inclusive, or
  a radical selected from

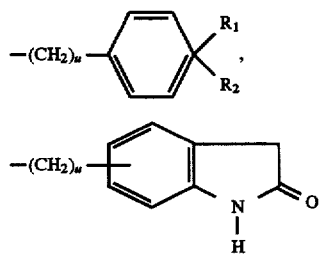

and

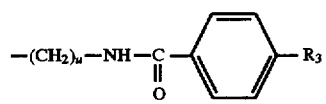

wherein
u represents an integer of from 1 to 6 inclusive;
$R_1$ represents a hydrogen or halogen atom, a hydroxy radical or an alkyl or alkoxy radical each containing from 1 to 6 carbon atoms inclusive in straight or branched chain;
$R_2$ represents a halogen atom, a hydroxy radical, an alkyl or alkoxy radical each containing from 1 to 6 carbon atoms inclusive in straight or branched chain, a phenyl radical or a group of the formula NHCOO—$C(CH_3)_3$, $NH_2$, NH—$COCH_3$, $NHCOCF_3$ $NHSO_2CH_3$ or

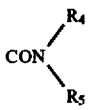

wherein $R_4$ and $R_5$, which are identical or different, each represents a hydrogen atom or a straight-chain or branched ($C_1$–$C_6$)alkyl radical; and
$R_3$ represents a halogen atom or a hydroxy, straight-chain or branched ($C_1$–$C_5$)alkoxy, trifluoromethyl, cyano, phenyl, p-aminophenyl or p-acetylphenyl radical;
in racemic form or in the form of optical isomers,
and the addition salts thereof with a pharmaceutically acceptable acid.

The prior art is illustrated especially by the Patent Specifications EP 0 286 515 and 0 286 516 which relate, inter alia, to 5,6,7,8-tetrahydronaphtho[2,3-b]furan amine compounds that behave like dopaminergic substances and have an antidepressant, anti-aggressive and psycho-stimulating activity.

Research carried out in the departments of the Applicant has demonstrated that, by modifying on the one hand the substituents of the amine function and on the other hand the nature of the A—D—E chain, a reinforcement of the dopaminergic properties of those products has been possible while making them more specific and selective, enabling the said products to have reduced side effects.

Currently, the substances used therapeutically for the treatment of disorders in which the dopaminergic system is implicated are not selective and all bind very strongly to the $D_2$ receptor, whether they are dopaminergic blockers (used in disorders associated with hyperactivity of that neurotransmitter as occur, for example, in schizophrenia) or dopaminergic activators (used in disorders associated with hypoactivity as occur in Parkinson's disease, for example). However, those $D_2$ dopaminergic blockers or activators have numerous side effects: tardive dyskinesia, hyperprolactinaemia, amenorrhoea in the case of the former, and cardiovascular and motor effects in the case of the latter.

The recent discovery of a new dopamine receptor, called the $D_3$ receptor, the concentration of which is very significant in the limbic system but very low in the nigrostriated nucleus and in the lactotrophic cells, encourages research into new medicaments that act on the dopaminergic system but that have as a preferential target the $D_3$ receptor and are thus exempt from the side effects typically associated with the $D_2$ receptor as mentioned above.

The structural modifications of the products of the prior art mentioned above have resulted in the compounds forming the subject of the present invention, which differ from the products of the Patent Specifications EP 0 286 515 and 0 286 516 both in their chemical structure and in their pharmacological and therapeutic properties.

Indeed, studies carried out in vitro (binding to cloned $D_2$ and $D_3$ receptors) with the compounds of the present invention demonstrate that the latter behave like ligands that have a high affinity for the $D_3$ dopaminergic receptors while having little affinity for the $D_2$ dopaminergic receptors, which is not true of the compounds forming the subject of the Patent Specifications EP 0 286 515 and 0 286 516.

That selectivity makes the compounds of the present invention valuable especially for use as medicaments that act on the dopaminergic system in Parkinson's disease (J. Neur. Transm., 1993, 94, 11–19), memory disorders (Nature, 1990, 347, 146–151), drug abuse (Science, 1993, 260, 1814), depression and as antipsychotics.

The present invention relates also to a process for the preparation of compounds of formula I which is characterised in that:

a secondary amine of formula II:

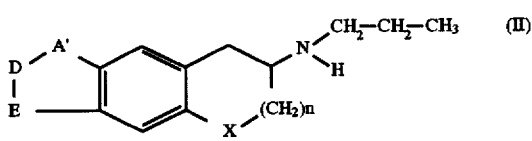

wherein

X and n are as defined above and

A'—D—E represents: $(CH_2)_3$, $(CH_2)_4$, —S—$(CH_2)_2$— or —S—CH=CH—, is reacted with a compound of formula III:

G—Y—Z     (III)

wherein:

Y and Z are as defined above and

G represents a halogen atom, a mesyloxy radical or a tosyloxy radical and the compounds of formula IV so obtained:

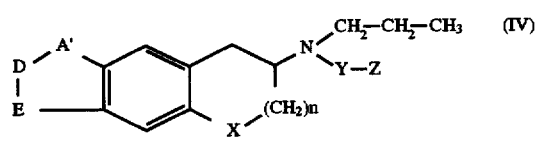

wherein:

—A'—D—E, X, n, Y and Z are as defined above are oxidized by means:

either of Jones reagent or of 2,3-dichloro-5,6-dicyano-1,4-benzoquinone in acetic acid and water when —A'—D—E— represents $(CH_2)_3$ or $(CH_2)_4$, or of hydrogen peroxide when —A'—D—E— represents —S—$(CH_2)_2$— or —S—CH=CH—, to obtain the compounds of formula Ia:

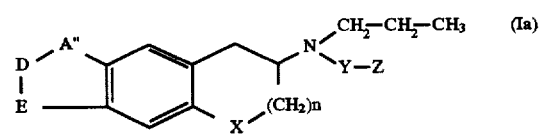

wherein:

X, n, Y and Z are as defined above and

A"—D—E represents a chain selected from:

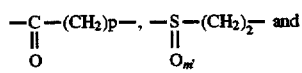
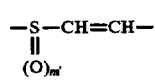

wherein m' represents 1 or 2, and p is as defined above;

and, when A"—D—E represents

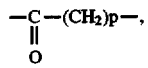

the corresponding compounds of formula Ia [that is to say, the compounds corresponding more specifically to formula I'a:

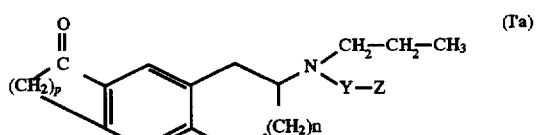

wherein p, X, n, Y and Z are as defined above] are reduced to obtain the compounds of formula Ib:

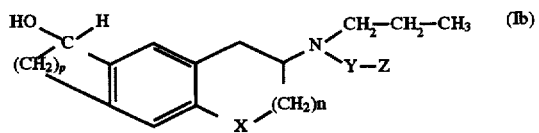

wherein p, X, n, Y and Z are as defined above.

The totality of the compounds of formula IV in which the meaning of A'—D—E is restricted to —S—$(CH_2)_2$— or —S—CH=CH—, and of the compounds of formulae Ia and Ib, form the totality of the compounds of formula I.

The condensation of compounds of formulae II and III is advantageously carried out in the presence of $K_2CO_3/CH_3CN$, $K_2CO_3/H_2O$, or $Na_2CO_3/CH_3COCH_3$.

The reduction of compounds of formula I'a is especially expediently carried out using $LiAlH_4$, $NaBH_4$ or $ZnBH_4$ as reducing agent.

Furthermore, compounds of formula I wherein Y represents solely $CH_2$, that is to say compounds corresponding more specifically to formula I':

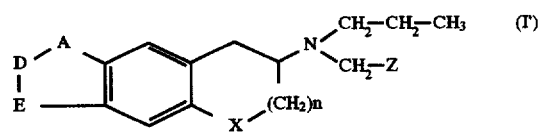

wherein A—D—E, X, n and Z are as defined for formula I, have likewise been prepared in accordance with the specific process below.

The present invention relates also to a process for the preparation of compounds of formula I':

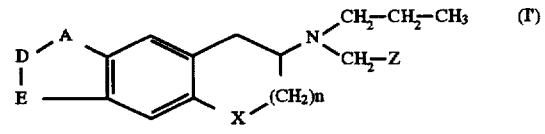

wherein A—D—E, X, n and Z are as defined above, characterised in that a secondary amine of formula II defined above is reacted:

either with a compound of formula V:

wherein Z is as defined above, which is carried out in a reductive medium, for example in the presence of sodium triacetoxyborohydride in acetic acid;

or with a compound of formula VI:

  (VI)

wherein Z is as defined above, and the resulting compound of formula VII:

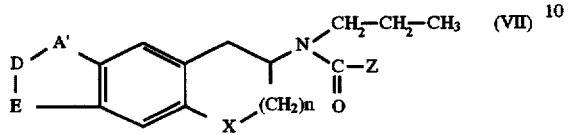  (VII)

wherein A'—D—E, X, n and Z are as defined above, is reduced to obtain, whichever reaction route is used, a compound of formula VIII:

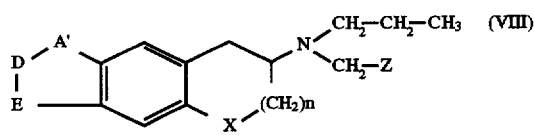  (VIII)

wherein A'—D—E, X, n and Z are as defined above;

which compound of formula VIII is then converted (as was the compound of formula IV above) by oxidation by means:
either of Jones reagent, or of 2,3-dichloro-5,6-dicyano-1,4-benzoquinone in acetic acid and water when A'—D—E represents $(CH_2)_3$ or $(CH_2)_4$,
or of hydrogen peroxide when —A'—D—E— represents —S—$(CH_2)_2$— or —S—CH=CH,
to obtain the compounds of formula I"a:

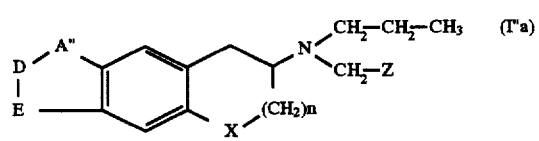  (I"a)

wherein A"—D—E, X, n and Z are as defined above, and, when A"—D—E represents

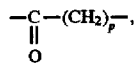

the corresponding compounds of formula I"a [that is to say the compounds corresponding more specifically to formula I'"a:

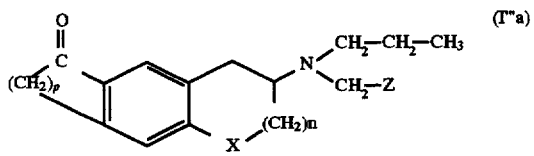  (I'"a)

wherein p, X, n and Z are as defined above] are reduced to obtain the compounds of formula I'b:

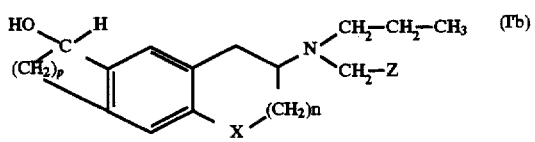  (I'b)

wherein p, X, n and Z are as defined above.

The totality of the compounds of formula VIII in which the meaning of A'—D—E is restricted to —S—$(CH_2)_2$— or —S—CH=CH—, and of the compounds of formulae I"a and I'b, form the totality of the compounds of formula I'.

The condensation of compounds of formulae II and VI is advantageously carried out in the presence of $Na_2CO_3$, $H_2O$ and $CH_3$—$COOC_2H_5$. The reduction of the compounds of formula VII is carried out satisfactorily with borane-dimethyl sulphide [$BH_3 \cdot S(CH_3)_2$] in tetrahydrofuran.

Furthermore, compounds of formula I wherein —A—D—E— represents solely —S—CH=CH—, that is to say compounds corresponding more specifically to formula I":

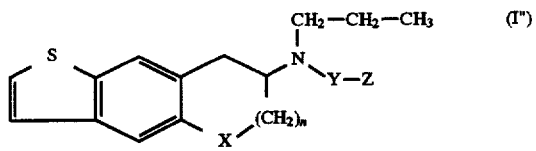  (I")

wherein X, n, Y and Z are as defined above, have likewise been prepared in accordance with the following scheme:

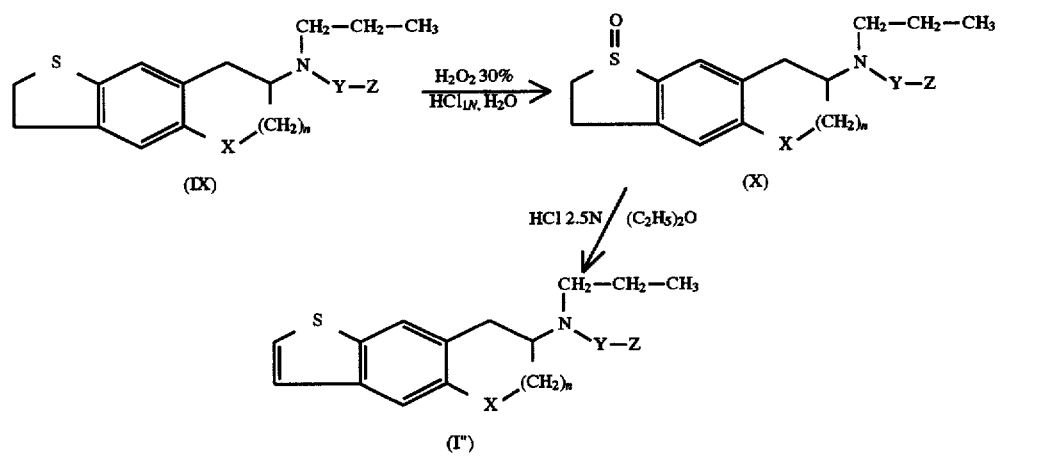

On the other hand, compounds of formula I wherein —A—D—E— represent solely

—C—(CH₂)₂—,
‖
O that is to say compounds corresponding more specifically to formula I''':

(I''')

wherein X, n, Y and Z are as defined above,
have likewise advantageously been prepared in accordance with the process below, which also forms part of the present invention.

The present invention thus relates also to a process for the preparation of compounds of formula I''':

(I''')

wherein X, n, Y and Z are as defined above,
which is characterised in that:
compounds of formula XI:

(XI)

wherein X, n, Y and Z are as defined above, and
Hal represents a halogen atom, and more especially a bromine or iodine atom, are treated
with methyl acrylate in dimethylformamide in the presence of palladium acetate, tri-o-tolylphosphine and triethylamine,
to yield compounds of formula XII:

(XII)

wherein X, n, Y and Z are as defined above,
which are reduced with hydrogen in the presence of platinum-on-carbon to yield the compounds of formula XIII:

(XIII)

wherein X, n, Y and Z are as defined above,
which are treated with sodium hydroxide solution to yield the compounds of formula XIV:

(XIV)

wherein X, n, Y and Z are as defined above,
which are cyclised by the action of phosphoric anhydride to obtain the compounds of formula I''' defined above.

The optically active forms of the compounds of formula I have been obtained either from the optically active forms of the starting materials of formula II, or by splitting the racemic forms of the compounds of formula I, according to methods known from the literature.

The salts of the compounds of formula I with pharmaceutically acceptable acids have been obtained according to conventional methods as indicated in the Examples hereinafter.

The starting materials of formula II are obtained according to the methods described hereinafter for the preparation of the starting materials for the products of the Examples.

The present invention relates also to pharmaceutical compositions containing as active ingredient a compound of formula I or a physiologically acceptable salt thereof, mixed with or associated with one or more appropriate pharmaceutical excipients.

The pharmaceutical compositions so obtained are generally presented in dosage form containing from 0.5 to 25 mg of active ingredient. They may, for example, be in the form of tablets, dragées, gelatin capsules, suppositories or injectable or drinkable solutions and may be administered by the oral, rectal or parenteral route.

The dosage may vary according to the age and weight of the patient, the administration route, the nature of the disorder and associated treatments, and ranges from 0.5 to 25 mg of active ingredient from 1 to 3 times per day.

The following Examples, which are given as non-limiting examples, illustrate the present invention.

The melting points have been determined either using a Kofler hot plate (K), or a hot plate under a microscope (MK).

The proton nuclear magnetic resonance spectra (NMR) have been carried out at 200 MHz.

Synthesis of the starting materials

The starting materials used in the following Examples have been prepared as follows:

Preparation 1

(3RS)-3-(N-propylamino)cyclopenta[g]3,4-dihydro-2H-benzopyran hydrochloride

Step A: (3RS)-3-nitrocyclopenta[g]2H-benzopyran

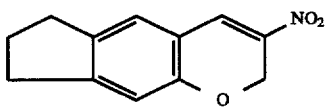

34.7 g (214 mmol) of 6-hydroxyindane-5-carboxaldehyde [described in J.A.C.S 1955, 77, 2466–75], 36.7 g (342.3 mmol) of industrial nitroethanol (85% strength), 17.7 g (107 mmol) of di-n-butylamine hydrochloride and 430 ml of isoamyl acetate are mixed together at room temperature, heated at reflux for 24 h and then left to cool. The solid which has formed is filtered off and washed with ethyl acetate and the filtrates are combined and evaporated to dryness. The residue is taken up in 500 ml of dichloromethane and washed with 200 ml of water, 200 ml of N sodium hydroxide solution (twice) and 200 ml of water, and then dried over magnesium sulphate. After evaporation, followed by flash chromatography on 1.5 kg of silica (eluant: dichloromethane), 11.3 g of the desired compound are obtained in the form of an orange solid. M.p. (K): 156° C. Yield: 24%.

Step B: (3RS)-3-nitrocyclopenta[g]3,4-dihydro-2H-benzopyran

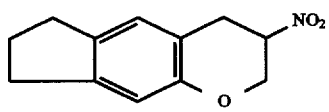

To 11.3 g (51.6 mmol) of the compound obtained in the preceding Step dissolved in a mixture of 330 ml of chloroform and 110 ml of isopropanol, there are added with vigorous stirring, 24.5 g of silica (Merck 230–400 mesh) in one go, and then, over a period of 15 min., 4.7 g (124.2 mmol) of sodium borohydride in portions. The whole is stirred at room temperature for 30 min., then the reaction is stopped by the addition of 8.5 ml of acetic acid. The mixture is stirred for a further 15 min., then filtered through sintered glass and washed thoroughly with dichloromethane. The combined filtrates are evaporated to yield 11.8 g of the expected nitro compound in the form of a yellow solid. M.p. (K): 141° C. Quantitative yield.

Step C: (3RS)-3-aminocyclopenta[g]3,4-dihydro-2H-benzopyran

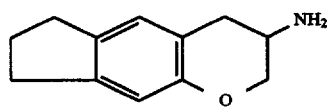

35.2 g (538 mmol) of powdered zinc are added to 11.8 g (53.8 mmol) of the compound obtained in the preceding Step dissolved in 270 ml of acetic acid. The whole is heated at 100° C. for 45 min., then cooled, and the zinc is filtered off and washed thoroughly with dichloromethane. After evaporation of the filtrates, the residue is taken up in 250 ml of dichloromethane and extracted with 60 ml of N hydrochloric acid (3 times), and the aqueous acidic phases are combined, rendered basic in the cold with concentrated sodium hydroxide solution, and then extracted with 100 ml of dichloromethane (twice). The combined organic phases are dried over magnesium sulphate and then concentrated to yield 3.45 g of the expected amine in the form of a beige solid. M.p. (K): 61°–63° C. Yield: 34%.

During the acid-base transition, a white insoluble product was formed. It was filtered and dried and then characterised as being the hydrochloride of the expected amine.

Step D: (3RS)-3-propionamidocyclopenta[g]3,4-dihydro-2H-benzopyran

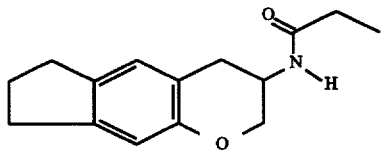

To 8.5 g (45 mmol) of the amine obtained in the preceding Step in 215 ml of ethyl acetate there are added at room temperature 215 ml of an aqueous 10% sodium carbonate solution then 5.85 ml (67 mmol) of propionyl chloride dropwise; the whole is then stirred for the night at room temperature. The white solid formed is filtered through sintered glass, washed with water and dried in vacuo to yield 7.16 g of the expected amide. M.p. (K): 162° C. Yield: 65%.

Step E: Title product 7 g (28.6 mmol) of the compound obtained in Step D are dissolved in 80 ml of tetrahydrofuran. 13.56 ml of borane-dimethyl sulphide (143 mmol) are poured in dropwise and the whole is heated at reflux for 20 h, cooled, and then 30 ml of CH₃OH are added and the whole is heated at reflux again for 3 h. The solvents are evaporated off and the residue is taken up in 150 ml of 1N HCl and 150 ml of ether. The precipitate is filtered off and washed with ether. 6.05 g of the expected product are obtained. M.p. (K):>260° C. Yield: 80%.

Preparation 2

(3RS)-3-(N-propylamino)cyclohexa[g]3,4-dihydro-2H-benzopyran hydrochloride

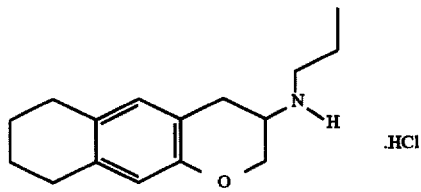

By proceeding as described for Preparation 1, Steps A to E, but using 5,6,7,8-tetrahydro-3-hydroxynaphthalene-2-carboxaldehyde (cf. J.A.C.S. 1958, 80, 3294–3300) in Step A instead of 6-hydroxyindane-5-carboxaldehyde, the expected hydrochloride is obtained. M.p. (K):>260° C.

Preparation 3

(3RS)-3-(N-propylamino)-6-oxocyclopenta[g]3,4-dihydro-2H-benzopyran

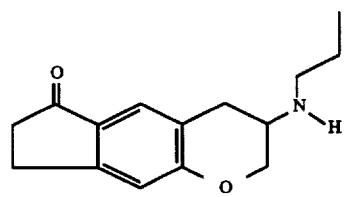

1 g (3.7 mmol) of the title compound of Preparation 1 is suspended in 15 ml of acetone at 0° C. 3.7 ml of Jones reagent are added dropwise while maintaining the temperature below 4° C., then the whole is stirred at room temperature for 4 h. The mixture is cooled to 0° C. again, 2 ml of isopropartol are added and the whole is stirred for the night at room temperature. The salts are filtered off and the organic phase is evaporated. The residue is taken up in 25 ml of 0.5N HCl and washed twice with 30 ml of ether each time. The aqueous acidic phase is rendered basic with concentrated NaOH and then extracted with ether. After washing and drying the organic phase, 500 mg of the desired compound are obtained. M.p. (K): 84° C. Yield: 78%.

NMR (CDCl₃/TMS): 7.5 (s, 1H); 6.8 (s,1H); 4.25 (dd, 1H); 4.0 (s, 1H); 3.15 (m, 1H); 3.0 (d,2H); 2.8 to 2.6 (m,6H); 1.7 (unresolved peak exchangeable with D₂O); 1.5 (m,2H); 0.95 (t,3H).

Preparation 4

(7RS)-7-(N-propylamino)-2,3,5,6,7,8-hexahydronaphtho[2,3-b]thiophene hydrochloride

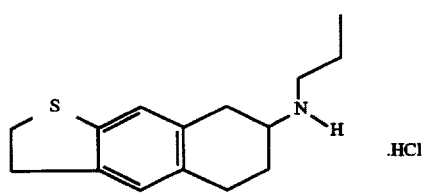

Step 1: 2,3,5,6,7,8-hexahydro-7-hydroxyimino-8-oxonaphtho[2,3-b]thiophene

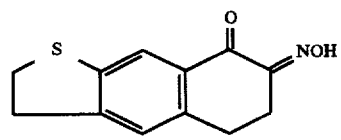

In a 4-liter, three-necked flask fitted with a mechanical stirring device and a nitrogen inlet, 53.2 g (474 mmol) of tert-potassium butanolate are suspended in 724 ml of dry ethyl ether. 95 ml of tert-butyl alcohol and 95 ml of ethyl alcohol are added in succession to that solution at room temperature. The solution obtained is heated at reflux for 1 h and then cooled to 3° C. At that temperature isoamyl nitrite (95 ml), and 2,3,5,6,7,8-hexahydro-8-oxonaphtho[2,3-b]thiophene [prepared according to W. Carruthers et al.; J Chem. Soc., 1962, p 704-708] (77.38 g, 379 mmol) dissolved in an ethyl ether/tetrahydrofuran mixture (1500 ml/200 ml), are added in succession thereto. After 0.5 h stirring at 3°-5° C., the reaction mixture is rapidly filtered under nitrogen. The precipitate is washed once with anhydrous ethyl ether and rapidly added in portions, while stirring vigorously, to an aqueous 1N HCl solution cooled with a water/ice bath. The precipitate is filtered off, washed with water and dried in vacuo to yield a dark-coloured powder: 59.3 g. Yield: 67%.

Step 2: 2,3,5,6,7,8-hexahydro-7-(N-propionamido)-8-oxonaphtho[2,3-b]thiophene

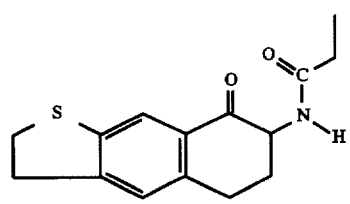

In a 3-liter three-necked flask fitted with a mechanical stirring device, 59 g (82.9 mmol) of the oxime obtained in the preceding Step are dissolved in 800 ml of a 1/1 mixture of propionic acid and propionic anhydride. After 20 minutes' stirring at room temperature, 67 g of zinc are added in portions (1 h). 30 min. after the addition is complete, the reaction mixture is diluted with 250 ml of CH₂Cl₂ and then filtered. The precipitate is washed with 250 ml of CH₂Cl₂ and then filtered and the filtrate is concentrated in vacuo to yield 137 g of a dark red solid. Purification of the latter by chromatography on silica (CH₂Cl₂/ethyl acetate: 90/10) enables 35 g of the expected product to be obtained. M.p. (K): 158°–160° C. Yield: 50%.

Step 3: 2,3,5,6,7,8-hexahydro-7-(N-propionamido)-8-hydroxynaphtho[2,3-b]thiophene

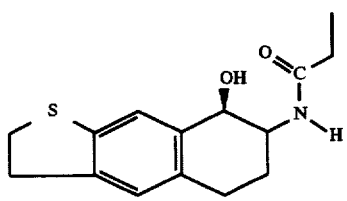

In a 4-liter three-necked flask fitted with a mechanical stirring device and a nitrogen inlet, 3.8 g (99.5 mmol) of AlLiH₄ are suspended in 850 ml of dry tetrahydrofuran at -78° C., and 22.8 g (253 mmol) of the product obtained above dissolved in 1060 ml of dry tetrahydrofuran are slowly added while maintaining the temperature of the reaction mixture below -70° C. After 2 hours' stirring at -78° C., 2.5 ml of a saturated aqueous solution of NH₄Cl are slowly added and the reaction mixture is brought to room temperature. The precipitate is filtered off and washed copiously with tetrahydrofuran. The filtrate is concentrated in vacuo. The residue (dark-coloured meringue) is purified by chromatography on silica (eluant: CH₂Cl₂/ethyl acetate: 90/10) to yield 15 g of the expected product. Yield: 65%.

Step 4: 2,3,5,6,7,8-hexahydro-7-(N-propionamido)naphtho[2,3-b]thiophene

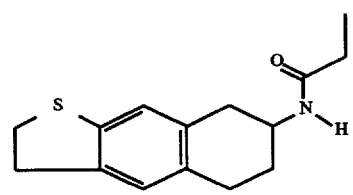

In a 500 ml three-necked flask fitted with a stirring device, a condenser and a nitrogen inlet, 3 g (10.8 mmol) of the product prepared in the preceding Step are suspended in 72 ml of CCl₄; 72 ml of triethylsilane hydride and then 35 ml of trifluoroacetic acid are added and the reaction mixture is heated to reflux. After 18 hours' stirring at reflux, the reaction mixture is concentrated in vacuo. The residue is taken up in 100 ml of acetonitrile and 100 ml of hexane. The hexane phase is extracted three times with 50 ml of acetonitrile each time. The acetonitrile phases are combined, washed once with 50 ml of hexane and concentrated in vacuo. The residue is purified by chromatography on silica (eluant: CH₂Cl₂/ethyl acetate: 90/10) to yield 2.19 g of the expected product. M.p. (K): 150°–152° C. Yield: 83%.

Step 5: Title product

In a 250 ml two-necked flask fitted with a stirring device, a condenser and a nitrogen inlet, 2.16 g (8.27 mmol) of the amide obtained in the preceding Step are dissolved in 95 ml of dry tetrahydrofuran, and 8.3 g (8.3 mmol) of borane-dimethyl sulphide are slowly added at room temperature. After 18 hours' stirring at reflux, the reaction is stopped by the slow addition of methanol while cooling the reaction mixture with a water/ice bath. After 0.5 hour's stirring at room temperature, the reaction mixture is concentrated in vacuo. The residue is taken up in 150 ml of methanol and heated at reflux for 2 h in the presence of 0.5 ml of aqueous 37% HCl. That methanolic solution is concentrated in vacuo to yield 2.48 g of the expected product. M.p. (K): 240°–250° C. with decomposition. Quantitative yield.

Preparation 5

(2RS)-2-(N,N-dipropylamino)cyclopenta[g]1,2,3,4-tetrahydronaphthalene

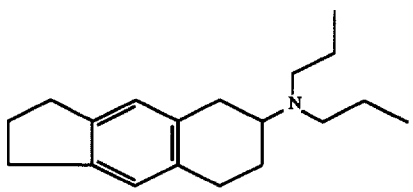

Step 1 :cyclopenta[f]indan-1-one

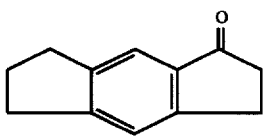

A mixture of 31 g (0.163 mol) of 3-(indan-5-yl)propionic acid and 154.9 g of polyphosphoric acid is heated for 1 h at 80° C. After cooling, the mixture is poured onto ice, stirred for one night, extracted with dichloromethane, washed, dried over MgSO$_4$ and evaporated. After purification on silica by flash chromatography with a CH$_2$Cl$_2$/cyclohexane mixture of 30/70 then 70/30, 6.5 g of the expected product are obtained. Yield: 23%.

Step 2: 1-aminomethylcyclopenta[f]indan-1-ol

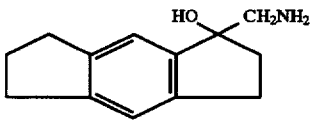

6 g (0.034 mol) of the product obtained in Step 1, 5.19 g (0.052 mol) of trimethylsilyl cyanide, 1.39 g of zinc iodide and 32.7 ml of 1,2-dimethoxyethane are introduced into an autoclave and the whole is heated at 60° C. for 4 days. After cooling, the solution obtained is added dropwise to a suspension of 2.55 g of lithium aluminium hydride in 70.4 ml of anhydrous glyme. When the addition is complete, the reaction mixture is heated to 60° C. Heating is continued for one night. The reaction mixture is then hydrolysed with 1.78 ml of water, 1.428 ml of 20% sodium hydroxide solution and finally with 6.5 ml of water. After filtration, the solvent is evaporated off and the residue is taken up in ether. An acid-base extraction yields 4.04 g of the expected product. Yield: 58.5%.

Step 3: 2-oxocyclopenta[g]1,2,3,4-tetrahydronaphthalene

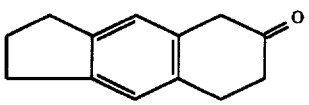

2 g (9.8 mmol) of the product obtained in the preceding Step are dissolved in 20 ml of a 25% acetic acid solution in water. After cooling to 0° C., a solution of 1.66 g of sodium nitrite in 7 ml of water is poured in dropwise. When the addition is complete, the mixture is allowed to return to room temperature and stirred for 3 h. After extraction of the reaction mixture with dichloromethane, the organic phase is washed with 0.1N sodium hydroxide solution and then with water. After drying and evaporation 1.4 g of the expected product are obtained. Yield: 76.7%.

Step 4: Title product 1.4 g (7.5 mmol) of the product obtained in the preceding Step, 50 ml of benzene and a spatula tip of para-toluenesulphonic acid are placed in a three-necked flask fitted with a Dean-Stark apparatus. The reaction mixture is heated to reflux and 3.53 g (34.6 mmol) of dipropyl-amine dissolved in 5 ml of benzene are added thereto. Refluxing is continued for 48 h. After evaporation of the benzene, 2.3 g of residue are obtained which are immediately taken up in 23 ml of ethanol and 10 ml of acetic acid. After the addition of 0.23 g of 10% palladium-on-carbon, the reaction mixture is hydrogenated at room temperature under atmospheric pressure, filtered, evaporated and, after acid-base treatment, yields 0.49 g of the expected product. Yield: 21%.

EXAMPLE 1

(3RS)-3-(N,N-dipropylamino)-6-oxocyclopenta[g]3,4-dihydro-2H-benzopyran

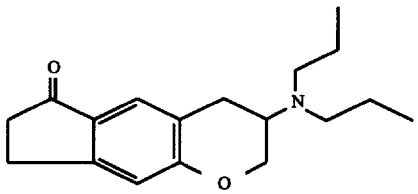

and its hydrochloride

Step 1 :(3RS)-3-(N,N-dipropylamino)cyclopenta[g]3,4-dihydro-2H-benzopyran

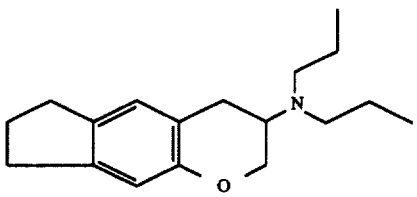

1.39 g of K$_2$CO$_3$ are added to 0.9 g (3.89 mmol) of the free base corresponding to the hydrochloride obtained in Preparation 1 dissolved in 20 ml of acetonitrile. 0.5 ml (5.05 mmol) of 1-iodopropane are then poured in and the whole is heated at reflux for 24 h, filtered, and the solvent is evaporated off. The residue is taken up in concentrated sodium hydroxide solution and extracted with methylene chloride to yield 0.7 g of the expected product in the form of an oil. Yield: 64%.

Step 2: Title product

At 0° C., 19.4 ml of Jones reagent are added dropwise to 5.3 g (19.4 mmol) of the amine obtained in the preceding Step in 70 ml of acetone, and then the whole is stirred for 20 h at room temperature. The temperature is brought back to 0° C., 10 ml of isopropanol are added dropwise, and the whole is then stirred at room temperature for 6 hours. The chromium salts are filtered through sintered glass, washed with acetone, and the filtrates are concentrated. The residue is taken up in 130 ml of 0.5N hydrochloric acid, washed with 140 ml of ether (twice), then rendered basic in the cold with concentrated sodium hydroxide solution. The whole is extracted with ether, and the combined organic phases are washed with water, dried over magnesium sulphate and concentrated to yield 3.44 g of the expected amine. Yield 62%.

0.23 g of that amine is dissolved in an ether/tetrahydrofuran mixture. 0.25 ml (1.1 eq.) of 2.5N ethereal hydrogen chloride is added, and the resulting solid is filtered off, washed with ether and dried in vacuo to yield 0.23 g of the hydrochloride. M.p. (MK): 161°–164° C. Yield: 89%.

NMR (DMSO-d6/TMS): 10.95 (unresolved peak exchangeable with $D_2O$); 7.5 (s,1H); 7.0 (s,1H); 4.65 (m,1H); 4.5 (m,1H); 3.9 (m,1H); 3.4 (m,2H); 2.9 to 3.2 (m,6H); 2.6 (t,2H); 1.75 (m,4H); 0.9 (t,6H).

EXAMPLE 2

(3RS)-3-(N-propyl-N-isopentylamino)-6-oxocyclopenta[g]3,4-dihydro-2H-benzopyran

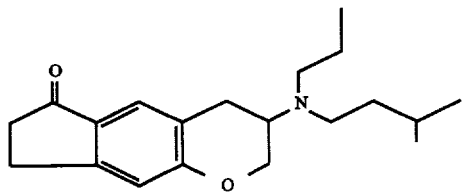

and its hydrochloride

The hydrochloride of the title product is obtained by proceeding as described in Example 1, but using 1-iodo-4-methylbutane instead of 1-iodoproparte in Step 1. M.p. (MK): 88°–91° C.

NMR (DMSO-d6/TMS): 11.05 (unresolved peak exchangeable with $D_2O$); 7.5 (s,1H); 7.0 (s,1H); 4.7 (m,1H); 4.5 (m,1H); 3.9 (m,1H); 3.0 to 3.5 (m,8H); 2.65 (t,2H); 1.5 to 1.9 (m,5H); 0.9 (d+t,9H).

EXAMPLE 3

(3RS)-3-(N,N-dipropylamino)-6-oxocyclohexa[g]3,4-dihydro-2H-benzopyran

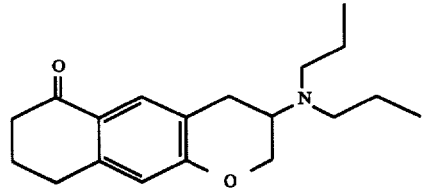

and its hydrochloride

The hydrochloride of the title product is obtained by proceeding as described in Example 1, but using the product obtained in Preparation 2. M.p. (MK): 181°–184° C.

NMR (DMSO-d6/TMS): 10.85 (unresolved peak exchangeable with $D_2O$); 7.75 (s,1H); 6.8 (s,1H); 4.65 (dd,1H); 4.4 (dd,1H); 3.85 (m,1H); 3.0 to 3.4 (m,6H); 2.9 (t,2H); 2.5 (t,2H); 2.0 (m,2H); 1.75 (m,4H); 0.9 (t,6H).

EXAMPLE 4

(7RS)-7-(N,N-dipropylamino)-2,3,5,6,7,8-hexahydronaphtho[2,3-b]thiophene

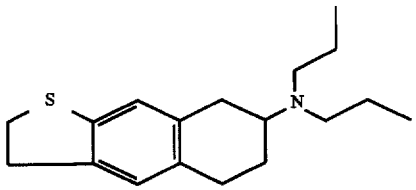

and its hydrochloride

Step 1:(TRS)-7-(N-propyl-N-propionamido)-2,3,5,6,7,8-hexahydronaptho[2,3-b]thiophene

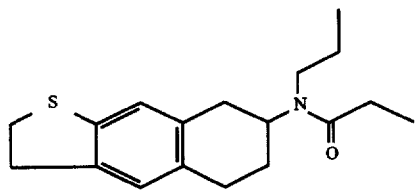

In a 250 ml three-necked flask fitted with a mechanical stirring device, 2.4 g (8.46 mmol) of the amine hydrochloride obtained in Preparation 4 are suspended in 63 ml of ethyl acetate. 63 ml of an aqueous 5% solution of $Na_2CO_3$ are added at room temperature and the two phase mixture is stirred vigorously until dissolution is complete. 1.1 ml (12.7 mmol) of propionyl chloride are added to that two phase solution at room temperature. After 5 hours' stirring at room temperature, the organic and aqueous phases are separated and the aqueous phase is extracted three times with ethyl acetate. The organic phases are combined, dried over magnesium sulphate and concentrated to yield 2.51 g of the expected amide. Yield: 97%.

Step 2: Title product

In a 500 ml two-necked flask fitted with a magnetic stirring device, a condenser and a nitrogen inlet, 2.51 g (8.28 mmol) of the amide obtained in the preceding Step are dissolved in 95 ml of dry tetrahydrofuran. 8.28 ml (83 mmol) of borane-dimethyl sulphide are slowly added thereto at room temperature. After 24 hours' stirring at reflux, the reaction is stopped by the slow addition of methanol while cooling the reaction mixture with a water/ice bath. After 0.5 hour's stirring at room temperature, the reaction mixture is concentrated in vacuo. The residue is taken up in 100 ml of methanol and heated at reflux for 2 h in the presence of 0.5 ml of aqueous 37% HCl.

The methanolic solution is concentrated in vacuo and the residue is partitioned between 100 ml of ethyl ether and 100 ml of aqueous 1N NaOH. The aqueous phase is extracted four times with 60 ml of ethyl ether each time. The organic phases are combined, washed with brine, dried over magnesium sulphate and concentrated to yield 0.8 g of amine. The addition of ethereal hydrogen chloride to a solution of the latter in 10 ml of ethyl ether enables the hydrochloride of the title product to be obtained. M.p. (MK): 180°–183° C. Yield: 30%.

$^1$H NMR (DMSOd6/TMS), δ: 10.6 ($NH^+$), 7.05 (2s,2H); 3.6 (m,1H); 3.3–2.7 (m,10H); 2.3 (m,1H); 1.8 (m,5H); 0.9 (t,6H).

EXAMPLE 5

(7RS)-7-(N-isopentyl-N-propylamino)-2,3,5,6,7,8-hexahydronaphtho[2,3-b]thiophene

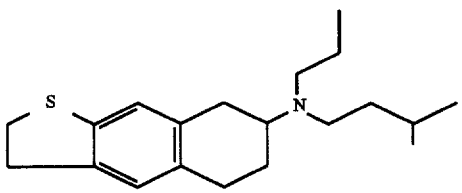

and its hydrochloride.

By proceeding as described in Example 4, but using isovaleric acid chloride instead of propionyl chloride, the expected product, the hydrochloride of which melts (MK) at 185° C., is obtained.

EXAMPLE 6

(3RS)-3-{N-[2-(cyclopropyl)ethyl]-N-propylamino}-6-oxocyclopenta[g]3,4-dihydro-2H-benzopyran

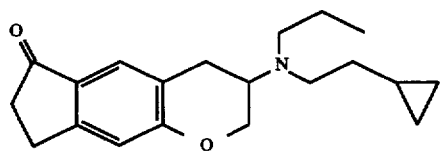

and its hydrochloride.

By proceeding as described in Example 4, but using the product of Preparation 3 and replacing the propionyl chloride with cyclopropylacetic acid chloride, the expected product, the hydrochloride of which melts (MK) at 87°–94° C., is obtained.

EXAMPLE 7

(3RS)-3-{N-[2-(p-hydroxyphenyl)ethyl]-N-propylamino}-6-oxocyclopenta[g]3,4-dihydro-2H-benzopyran

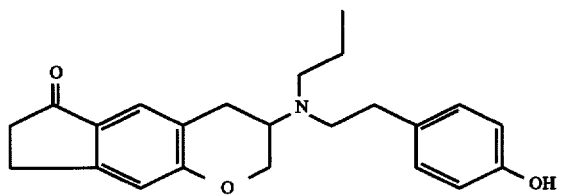

and its hydrochloride.

2 g (8.1 mmol) of the compound obtained in Preparation 3 and 2.03 g (10.1 mmol) of 1-bromo-2-(p-hydroxyphenyl) ethane are introduced into a suspension of 2.6 g (24.3 mmol) of sodium carbonate in 50 ml of acetone. The whole is heated at reflux for 24 h and then again 2.03 g of 1-bromo-2-(p-hydroxyphenyl)ethane are added and the mixture is again heated at reflux for 48 h. After evaporation to dryness, the residue is taken up in 100 ml of $CH_2Cl_2$, washed twice with 30 ml of water each time and then dried over $MgSO_4$. The residue is chromatographed on silica (eluant $CH_2Cl_2$/$CH_3OH$: 99/1) to yield 1.37 g of free base, which is converted into the hydrochloride by the addition of a 2N ethereal hydrogen chloride solution. 0.97 g of the expected hydrochloride is obtained. M.p. (MK): 122°–128° C. Yield: 29%.

1H NMR (DMSO d6/TMS) δ: 11.15 (unresolved peak exchangeable with $D_2O$); 9.35 (1H, exchangeable with $D_2O$); 7.5 (s,1H); 7.1 (d,2H); 7.05 (s,1H); 6.7 (d,2H); 4.7 and 4.5 (2m,2H); 4.0 (m,1H); 3.5 to 2.9 (m,10H); 2.6 (t,2H); 1.8 (m,2H); 0.9 (t,3H).

EXAMPLE 8

(3RS)-3-{N-[(2E)-but-2-enyl]-N-propylamino}-6-oxocyclopenta[g]3,4-dihydro-2-H-benzopyran

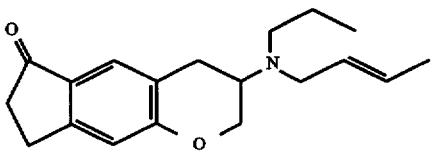

and its hydrochloride

By proceeding as described in Example 7, but using 4-bromobut-2-ene in trans form instead of 1-bromo-2-(p-hydroxyphenyl)ethane, the title product, the hydrochloride of which melts (MK) at 87°–91° C., is obtained.

EXAMPLE 9

(3RS)-3-{N-[2-((3H)-indol-2-on-4-yl)ethyl]-N-propylamino}-6-oxocyclopenta[g]3,4-dihydro-2H-benzopyran.

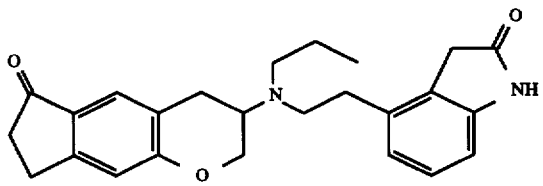

By proceeding as described in Example 7, but using 1-hydroxy 2-[(3H)-indol-2-on-4-yl]ethane tosylate instead of 1-bromo-2-(p-hydroxyphenyl)ethane, the expected product is obtained which melts (MK) at 190°–192° C.

EXAMPLE 10

(7RS)-7-{N-[3-(4-acetylaminophenyl)propyl]-N-propylamino}-2,3,5,6,7,8-hexahydronaphtho[2,3-b]thiophene

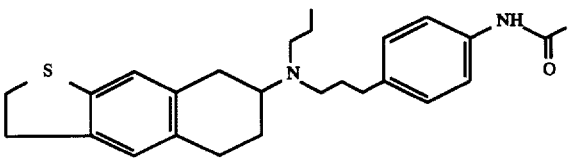

and its hydrochloride

By proceeding as described in Example 7, but using the product of Preparation 4 and replacing the 1-bromo-2-(p-hydroxyphenyl)ethane with 3-(4-acetylaminophenyl)-1-iodo-propane, the expected product, the hydrochloride of which melts (MK) at 130°–135° C., is obtained.

EXAMPLE 11

(7RS)-7-{N-(2-(4-acetylaminophenyl)ethyl]-N-propylamino}-2,3,5,6,7,8-hexahydro-naphtho[2,3-b]thiophene

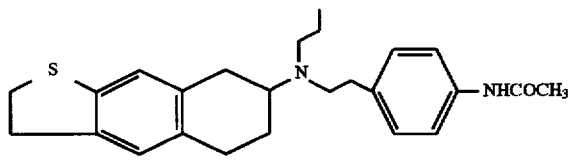

and its hydrochloride

By proceeding as described in Example 7, but using the product of Preparation 4 and replacing the 1-bromo-2-(p-hydroxyphenyl)ethane with 2-(4-acetylaminophenyl)-1-iodo-ethane, the expected product, the hydrochloride of which melts (MK) at 145°–150° C., is obtained.

and its hydrochloride 2.45 g (10.0 mmol) of the compound obtained in Preparation 3 and 2.7 g (10.0 mmol) of 4-(4-bromobenzamido) butyraldehyde are introduced into a mixture of 0.57 ml of acetic acid and 40 ml of 1,2-dichloroethane. While cooling at 10° C., 3.2 g (15 mmol) of sodium acetoxy-borohydride are added in portions, then the whole is left a room temperature for 48 h. After the addition of 50 ml of water, the phases are separated and the aqueous phase is back extracted twice with 50 ml of $CH_2Cl_2$ each time. The combined organic phases are dried over $MgSO_4$, concentrated and purified on silica using as eluant a $CH_2Cl_2/CH_3OH$ mixture, 98/2. 3.6 g of the expected product are obtained. The corresponding hydrochloride is prepared by the addition of a 1.8N ethereal hydrogen chloride solution. 3.74 g of hydrochloride are obtained, (yield: 69.9%) the melting point (MK) of which is 110°–115° C.

EXAMPLE 14

(7RS)-7-[N-[4-(4-bromobenzamido)butyl]-N-propylamino]-2,3,5,6,7,8-hexahydronaphtho-[2,3-b]thiophene

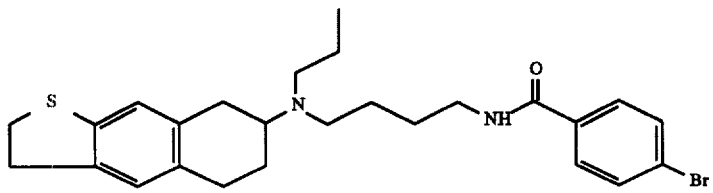

and its hydrochloride

By proceeding as described in the above Example, but using the product of Preparation 4 instead of that of Preparation 3, the desired product, the hydrochloride of which melts (MK) at 100°–110° C., is obtained.

EXAMPLE 12

(7RS)-7-{N-[3-(4-atninocarbonylphenyl)propyl]-N-propylamino}-2,3,5,6,7,8-hexahydro-naphtho[2,3-b]thiophene

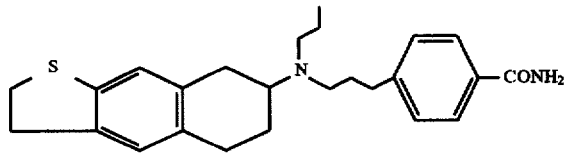

By proceeding as described in Example 7, but using the product of Preparation 4 and replacing the 1-bromo-2-(p-hydroxyphenyl)ethane with 3-(4-aminocarbonylphenyl) propan-1-ol mesylate, the expected product is obtained, which melts (MK) at 122°–124 ° C.

EXAMPLE 13

(3RS)-3-[N-[4-(4-bromobenzamido)butyl]-N-propylamino]-6-oxocyclopenta[g]3,4-dihydro-2H-benzopyran

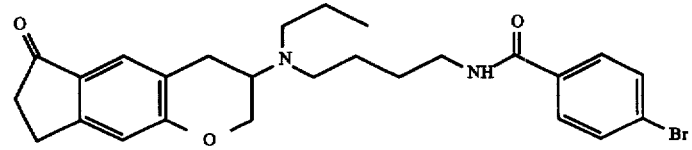

EXAMPLE 15

(7RS)-7-(N-pentyl-N-propylamino)-2,3,5,6,7,8-hexahydronaphtho[2,3-b]thiophene

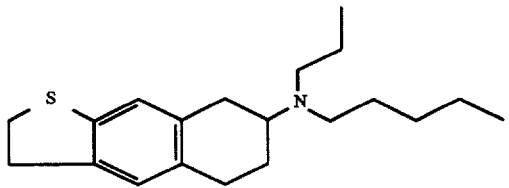

and its hydrochloride

By proceeding as described in the Example 13, but using the product of Preparation 4 and replacing the 4-(4-bromobenzamido)butyraldehyde with valeraldehyde, the

EXAMPLE 16

(7RS)-7-{N-[3-(4-tert-butoxycarbonylaminophenyl)propyl]-N-propylamino}-2,3,5,6,7,8-hexahydronaphtho[2,3-b]thiophene

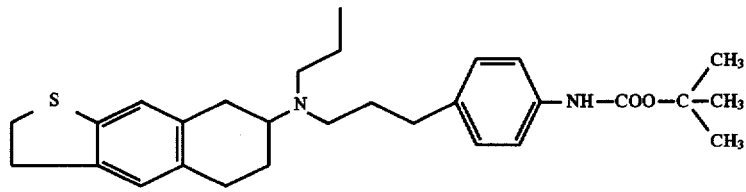

By proceeding as described in the Example 13, but using the product of Preparation 4 and replacing the 4-(4-bromobenzamido)butyraldehyde with 3-(4-tert-butoxycarbonylamino-phenyl)propionaldehyde, the desired product is obtained in the form of a meringue.

EXAMPLE 17

(7RS)-7-{N-[3-(4-aminophenyl)propyl]-N-propylamino}-2,3,5,6,7,8-hexahydronaphtho[2,3-b]thiophene

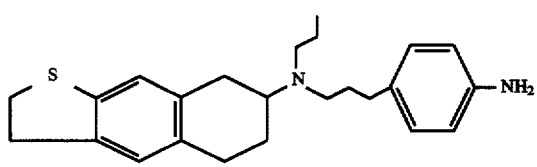

1.62 g of the product of the preceding Example (3.36 mmol) dissolved in 10 ml of methylene chloride is treated dropwise, at room temperature, with 2 ml of o-methoxyphenylthiol then 10 ml of trifluoroacetic acid. After 3 h at room temperature, the reaction mixture is concentrated in vacuo, and the residue is washed with ether and then taken up in water and washed once more with ether. The aqueous phase is rendered alkaline with normal sodium hydroxide solution and extracted with ether. After drying the organic phase, 0.86 g of the expected product is obtained in the form of a meringue (Yield: 67%).

EXAMPLE 18

(7RS)-7-{N-[3-(4-trifluoroacetylaminophenyl)propyl]-N-propylamino}-2,3,5,6,7,8-hexahydronaphtho[2,3-b]thiophene

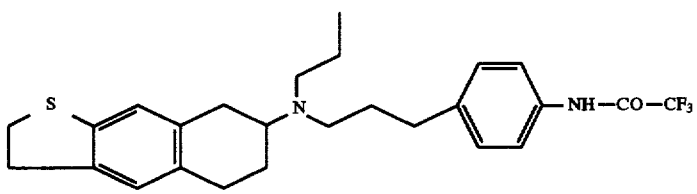

and its hydrochloride 0.43 g (1.13 mmol) of the product obtained in the preceding Example is treated at 0° C., in 11 ml of methylene chloride, with 0.18 ml of trifluoroacetic anhydride. After 30 minutes, the whole is diluted with a saturated sodium hydrogen carbonate solution and extracted with methylene chloride. After washing and drying the expected product, the whole of which is transformed into hydrochloride (0.37 g), MP (MK): 113°–120° C., is obtained.

EXAMPLE 19

(7RS)-7-{N-[3-(4-methylsulphonylaminophenyl)propyl]-N-propylamino}-2,3,5,6,7,8-hexahydronaphtho[2,3-b]thiophene

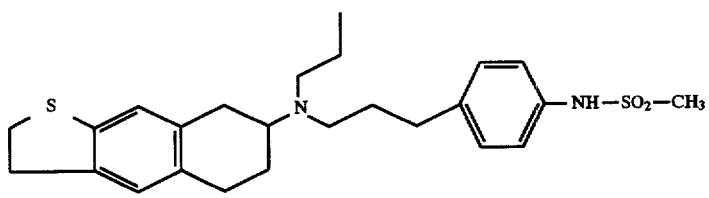

0.13 g (1.13 mmol) of the product obtained in the above Example 17 dissolved in 11 ml of methylene chloride is treated at 0° C. with 0.11 ml of mesyl chloride and 0.31 ml of triethylamine. After 1 h at room temperature, the mixture is diluted with a saturated solution of sodium hydrogen carbonate and extracted with methylene chloride. After washing and drying, the expected product, the whole of which is transformed into hydrochloride (0.15 g) Mp (MK): 137°–140° C., is obtained.

EXAMPLE 20

(7RS)-7-(N,N-dipropylamino )-1-oxocyclopenta[g]-5,6,7,8-tetrahydronaphthalene

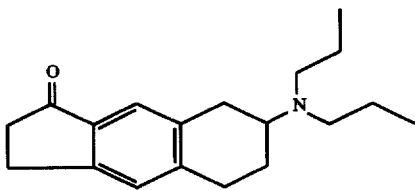

1st method

Using the method described in Step 2 of Example 1, but using the product of Preparation 5 instead of the product of Preparation 1 as starting material, the expected product is obtained after separation by HPLC (column KC18; mobile phase: $H_2O:CH_3CN:TFA/800:200:1$) and rendering basic and has a melting point (MK) of 66°–69° C.

2nd method

Step A: trans-3-[2-(N,N-dipropylamino)-1,2,3,4-tetrahydronaphth-6-yl]prop-2-enoic acid methyl ester 3.1 g (0.01 mol) of 6-bromo-2-(N,N-dipropylamino)-1,2,3,4-tetrahydronaphthalene are dissolved in 50 ml of dimethylformamide. There are added in succession to that solution 0.94 g (0.011 mol) of methyl acrylate, 22.4 mg (0.1 mmol) of palladium acetate, 121 mg (0.4 mmol) of tri-ortho-tolylphosphine and 1.6 ml (0.011 mol) of triethylamine. The mixture is heated at 125°–130° C. for 3 h 30 min. with stirring, cooled, poured into 700 ml of water, extracted with ethyl acetate and washed with a solution of LiCl. After acid to base change, 0.9 g of the expected product is obtained.

Step B: 3-[2-(N,N-dipropylamino)-1,2,3,4-tetrahydronaphth-6-yl]propionic acid methyl ester 2.1 g (6.6 mmol) of the product prepared in the preceding Step and 0.2 g of platinum oxide are introduced into 35 ml of methanol. Hydrogenation is carried out at atmospheric pressure and at room temperature for 18 h. The whole is filtered and concentrated to isolate 2 g of the expected product. Yield: 95%.

Step C: 3-[2-(N,N-dipropylamino)-1,2,3,4-tetrahydronaphth-6-yl]propionic acid 2.5 g (7.8 mmol) of the product obtained in the preceding Step, 20 ml of methanol and 8 ml of normal sodium hydroxide solution are placed in a two-necked flask. The whole is stirred at room temperature for 18 h, acidified with 8 ml of 1N HCl and concentrated. The product is taken up in acetonitrile, and insoluble material is filtered off and concentrated to yield, after drying, 2 g of the expected product in the form of a viscous oil. Yield: 85%.

Step D: Title product 20 g of polyphosphonic acid are heated to 75° C. 1.8 g (6 mmol) of the acid prepared in the above Step C are added in one go, and the whole is maintained at that temperature for 1 h. The mixture is cooled partially and ice is added. The whole is rendered basic with sodium hydroxide solution in the presence of ethyl acetate, dried and concentrated to yield 0.8 g of a residue which is purified by HPLC under conditions identical to those used in the first method. After rendering basic, 0.2 g of the expected product, which melts (MK) at 68°–70° C., is obtained.

NMR 300 MHz ($CDCl_3$/TMS) 7.5 (s,1H); 7.2 (s,1H); 3.1 (t,2H); 3.1 to 2.7 (m,5H); 2.7 (t,2H); 2.5 (m,4H); 2.1 to 1.6 (m,2H); 1.5 (m,4H); 0.9 (t,6H).

EXAMPLE 21

(7RS)-7-(N,N-dipropylamino)-1-oxo-2,3,5,6,7,8-hexahydronaphtho[2,3-b]thiophene.

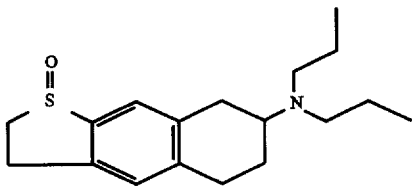

1.96 g (6 mmol) of the product obtained in Example 4, in the form of a hydrochloride dissolved in a mixture of 38 ml of water and 6 ml of 1N hydrochloric acid, is treated with 0.85 ml of 30% hydrogen peroxide. The mixture is heated at 80° C. for 30 minutes. After cooling, the reaction mixture is rendered alkaline and extracted with ether to yield, after evaporation, 1.81 g of residue which is purified by flash chromatography on a silica column (eluant $CH_2Cl_2$—MeOH/95–5) to give 1.28 g of the expected product in oily form. Yield: 70%.

NMR 200 MHz ($CDCl_3$/TMS) 7.65 (s,1H); 7.3 (s,1H); 3.8 to 3.5 (m,2H); 3.5 to 2.8 (m,1H); 2.35 (m,1H); 2.0 to 1.7 (m,5H); 0.85 (t,6H).

EXAMPLE 22

(7RS)-7-(N,N-dipropylamino)-5,6,7,8-tetrahydronaphtho[2,3-b]thiophene and its hydrochloride 1 g of the product prepared in the preceding Example is treated at room temperature with 20 ml of a 2.5N ethereal hydrogen chloride solution for 6 h. After rendering alkaline, the reaction mixture is chromatographed to yield 0.3 g of the expected product, the hydrochloride of which melts at 212°–215° C. (MK).

NMR (200 MHz CDCl$_3$) 12.5 (unresolved peak exchangeable with D$_2$O); 7.65 (s,1H); 7.55 (s,1H); 7.4 (d,1H); 7.25 (d,1H); 3.75 (m,1H); 3.5 to 2.9 (m,8H); 2.65 (m,1H); 2.3 to 1.9 (m,5H); 1.05 (t,6H).

EXAMPLE 23

Pharmacological study STUDIES OF THE BINDING OF THE COMPOUNDS OF THE INVENTION TO D$_2$ AND D$_3$ RECEPTORS The results are expressed in the form of pK$_i$ (pK$_i$=–logK$_i$).

The K$_i$ value is derived from the formula K$_i$=IC$_{50}$/(1+L/KD), where L is the concentration of [$^{125}$I]-iodosulpride used in the experiment and Kd its dissociation constant.

The IC$_{50}$, which represents the concentration that gives a 50% inhibition of the binding of the radioligand, is calculated by non-linear regression (Simplex method).

The products of the present invention demonstrate for the D$_3$ receptor affinities of which the pK$_i$ is between 7 and 9.

Furthermore, all of the products of the invention exhibit affinities for the D$_2$ receptor that are from 10 to 80 times lower than those exhibited for the D$_3$ receptor.

The products of the present invention thus behave like far more selective ligands than the reference aminotetralines (+) AJ 76 and (+) UH 232, the selectivities of which are only 2 and 5, respectively.

We claim:

1. A compound selected from the group consisting of those of formula I:

wherein:

—A—D—E— is selected from the group consisting of:

—C—(CH$_2$)$_p$—,   —CH—(CH$_2$)$_p$—,   —S—(CH$_2$)$_2$— and
∥                     |                    ∥
O                    OH                   (O)$_m$ —S—CH=CH—,
∥
(O)$_m$ wherein
p is selected from 2 or 3 and
m is selected from zero, 1 or 2;
X is selected from:
  —CH$_2$— and also, when —A—D—E— is selected from —C—(CH$_2$)$_p$—  or  CH—(CH$_2$)$_p$—,
∥                      |
O                     OH X may also represent oxygen;
n represent:
  zero or 1 when X represents CH$_2$ and
  solely 1 when X represents oxygen;
Y is selected from the group consisting of a single bond and —CH$_2$—, and
Z is selected from the group consisting of:
  alkyl, alkenyl, and alkynyl, each containing up to 10 carbon atoms inclusive in straight or branched chain and each unsubstituted or substituted by one or more substituent selected from the group consisting of cycloalkyl having from 3 to 7 carbon atoms inclusive, and —(CH$_2$)$_u$—⟨phenyl with R$_1$, R$_2$⟩, —(CH$_2$)$_u$—⟨indolinone-NH⟩ and

—(CH$_2$)$_u$—NH—C(=O)—⟨phenyl with R$_3$⟩ wherein
u represents an integer of from 1 to 6 inclusive;
R$_1$ is selected from the group consisting of hydrogen, halogen, hydroxy, alkyl, and alkoxy each containing 1 to 6 carbon atoms inclusive in straight or branched chain;
R$_2$ is selected from the group consisting of halogen, hydroxy, alkyl, and alkoxy each containing 1 to 6 carbon atoms inclusive in straight or branched chain, phenyl, and groups of formula: NHCOO—C(CH$_3$)$_3$, NH$_2$, NH—COCH$_3$, NHCOCF$_3$, NHSO$_2$CH$_3$, and

CON(R$_4$)(R$_5$)

wherein R$_4$ and R$_5$, which are identical or different, are each selected from hydrogen and straight-chain or branched (C$_1$–C$_6$)alkyl; and $R_3$ is selected from the group consisting of: halogen, hydroxy, straight-chain and branched ($C_1$–$C_5$)alkoxy, trifluoromethyl, cyano, phenyl, p-aminophenyl, and p-acetylphenyl;

in racemic form and in the form of optical isomers, and addition salts thereof with pharmaceutically-acceptable acids.

2. A compound of claim 1 which is selected from the group consisting of (7RS)-7-(N,N-dipropylamino)-2,3,5,6,7,8-hexahydronaphtho[2,3-b]thiophene and its hydrochloride.

3. A compound of claim 1 which is selected from the group consisting of (3RS)-3-{N-[2-(p-hydroxyphenyl)ethyl]-N-propylamino}-6-oxocyclopenta[g]3,4-dihydro-2H-benzopyran and its hydrochloride.

4. A compound of claim 1 which is (7RS)-7-(N-pentyl-N-propylamino)-2,3,5,6,7,8-hexahydronaphtho[2,3-b]thiophene.

5. A compound of claim 1 which is (7RS)-7-(N,N-dipropylamino)-1-oxocyclopenta[g]5,6,7,8-tetrahydronaphthalene.

6. A method for treating a living animal body afflicted with Parkinson's disease, a condition selected from memory disorders, disorders associated with drug abuse, depression, and psychotic states, comprising the step of administering to the said living animal body an amount of a compound of claim 1 which is effective for the alleviation of said condition.

7. A pharmaceutical composition useful in the treatment of a condition selected from Parkinson's disease, memory disorders, disorders associated with drug abuse, depression, and psychotic states, comprising as active ingredient at least one compound according to claim 1 together with one or more pharmaceutically-acceptable excipients.

* * * * *

UNITED STATES PATENT AND TRADEMARK OFFICE
CERTIFICATE OF CORRECTION

PATENT NO. : 5,726,208
DATED : March 10, 1998
INVENTOR(S) : J.L. Peglion, et al.

It is certified that error appears in the above-indentified patent and that said Letters Patent is hereby corrected as shown below:

Column 7, line 59: In the formula (top right hand side), "$CH_2-CH_2-CH_3(XIII)$" should read
-- $CH_2-CH_2-CH_3$ (XIII) --. The "(XIII)" is the number of the formula and should be spaced apart.

Column 15, line 42: "1-iodoproparte" should read
-- 1-iodopropane --.

Column 18, line 50: "(4-acetylatninophenyl)" should read -- (4-acetylaminophenyl) --.

Column 24, line 66: "(m,1H):" should read -- (m,11H); --

Column 25, line 28: "STUDIES OF THE...." should begin a new paragraph.

Column 26, line 27: Delete the word "from".
Page 1 of Preliminary Amendment, dtd 10/11/96, Claim 1, line 20 on page 33.

Column 26, line 48: Delete the word "from".
Page 1 of Preliminary Amendment, dtd 10/11/96, Claim 1, line 3 on page 34.

UNITED STATES PATENT AND TRADEMARK OFFICE
CERTIFICATE OF CORRECTION

PATENT NO. : 5,726,208
DATED : March 10, 1998
INVENTOR(S) : J.L. Peglion, B. Goument, J.C. Harmange, J. Vian, A. Dessinges, M. Millan, V. Audinot It is certified that error appears in the above-indentified patent and that said Letters Patent is hereby corrected as shown below:

Column 28, line 5: "a condition selected from" should be deleted from its present place and <u>inserted</u> before "Parkinson's".

Signed and Sealed this

Sixteenth Day of June, 1998

Attest:

BRUCE LEHMAN

Attesting Officer

Commissioner of Patents and Trademarks